(12) United States Patent
Novak et al.

(10) Patent No.: US 8,430,897 B2
(45) Date of Patent: Apr. 30, 2013

(54) ULTRASONIC WOUND DEBRIDER PROBE AND METHOD OF USE

(75) Inventors: Theodore A. D. Novak, Northport, NY (US); Christopher Bush, Commack, NY (US)

(73) Assignee: Misonix Incorporated, Farmingdale, NY (US)

( * ) Notice: Subject to any disclaimer, the term of this patent is extended or adjusted under 35 U.S.C. 154(b) by 577 days.

(21) Appl. No.: 11/511,856

(22) Filed: Aug. 29, 2006

(65) Prior Publication Data

US 2008/0058585 A1    Mar. 6, 2008

(51) Int. Cl.
*A61B 17/32*    (2006.01)
(52) U.S. Cl.
USPC ....................................................... 606/169
(58) Field of Classification Search .................. 606/169; 600/101
See application file for complete search history.

(56) References Cited

U.S. PATENT DOCUMENTS

| | | | | |
|---|---|---|---|---|
| 3,896,811 | A | * | 7/1975 | Storz .............................. 606/128 |
| 4,823,793 | A | * | 4/1989 | Angulo et al. ................ 606/128 |
| 6,482,216 | B1 | * | 11/2002 | Hiblar et al. .................. 606/159 |
| 6,578,581 | B1 | * | 6/2003 | Khalsa ........................... 128/898 |
| 6,723,110 | B2 | * | 4/2004 | Timm et al. ................... 606/169 |
| 7,025,735 | B2 | | 4/2006 | Soring et al. |
| 2001/0047182 | A1 | | 11/2001 | Banko |
| 2004/0030254 | A1 | | 2/2004 | Babaev |
| 2006/0241470 | A1 | | 10/2006 | Novak et al. |
| 2008/0004649 | A1 | | 1/2008 | Babaev |

FOREIGN PATENT DOCUMENTS

| GB | 2423931 A | * | 9/2006 |
|---|---|---|---|
| WO | WO/02/060525 | | 8/2002 |

\* cited by examiner

*Primary Examiner* — S. Thomas Hughes
*Assistant Examiner* — Julie A Szpira
(74) *Attorney, Agent, or Firm* — R. Neil Sudol; Coleman Sudol Sapone, P.C.

(57) ABSTRACT

An ultrasonic probe includes a shaft having a longitudinal axis and a head disposed at a distal end of the shaft. The head has a cylindrical lateral surface and an end face oriented perpendicularly to the axis. The head has three shaping surfaces at a distal end of the cylindrical surface, each shaping surface extending at an acute angle to the axis. Each of the shaping surfaces intersects or is contiguous with both the cylindrical surface and the end face.

33 Claims, 1 Drawing Sheet

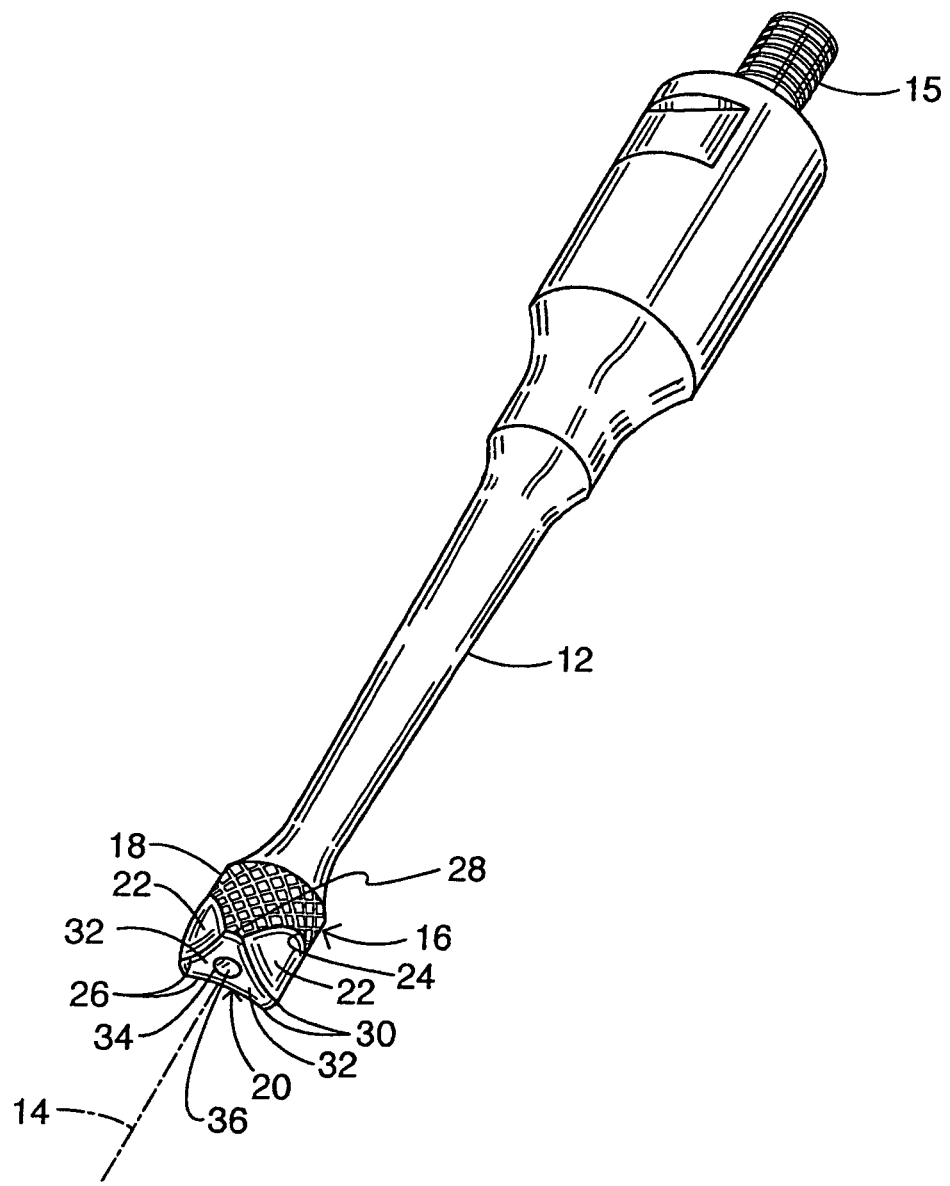

ULTRASONIC WOUND DEBRIDER PROBE AND METHOD OF USE

BACKGROUND OF THE INVENTION

This invention relates to ultrasonic surgical instruments and associated methods of use. More particularly, this invention relates to high-efficiency medical treatment probes for ultrasonic surgical aspirators. These probes increase the ability to fragment and emulsify hard and soft tissue in a clinical environment while reducing unwanted heat and collateral tissue damage.

Over the past 30 years, several ultrasonic tools have been invented which can be used to ablate or cut tissue in surgery. Such devices are disclosed by Wuchinich et al. in U.S. Pat. No. 4,223,676 and Idemoto et al in U.S. Pat. No. 5,188,102.

In practice, these surgical devices include a blunt tip hollow probe that vibrates at frequencies between 20 kc and 100 kc, with amplitudes up to 300 microns or more. Such devices ablate tissue by producing cavitation bubbles which implode and disrupt cells, by generating tissue compression and relaxation stresses (sometimes called the jackhammer effect), or by giving rise to other forces such as mechanical shearing and micro streaming of bubbles in the tissue matrix. The effect is that the tissue becomes fragmented and separated. It then becomes emulsified with the irrigant solution. The resulting emulsion is then aspirated from the site. Bulk excision of tissue is possible by applying the energy around and under an unwanted tissue mass to separate it from the surrounding structure. The surgeon can then lift the tissue out using common tools such as forceps.

The probe or tube is excited by a transducer of either the piezoelectric or magnetostrictive type that transforms an alternating electrical signal within the frequencies indicated into a longitudinal or transverse vibration. When the probe is attached to the transducer, the two become a single element with series and parallel resonances. The designer will try to tailor the mechanical and electrical characteristics of these elements to provide the proper frequency of operation. Most of the time, the elements will have a long axis that is straight and has the tip truncated in a plane perpendicular to the long axis, as shown in FIG. 1. This is done for simplicity and economic considerations. In almost all applications, whether medical or industrial, such an embodiment is practical and useful. However, in applications such as the debridement of burns, wounds, diabetic ulcers or ulcers induced by radiation treatments, the blunt straight probe has been shown to be less effective in removing the hard eschar buildup that occurs when the wound is healing. This eschar buildup must be removed so that the healthy tissue is exposed and allowed to close the wound to provide complete healing with minimal scar tissue formation. Also, the small diameter tip, since it is cannulated, has a small annular area with limits energy transmission into the wound. This extends the length of the procedure and causes operator fatigue and patient discomfort.

Therefore, it is desired to provide a probe that can be mated to an ultrasonic surgical aspirator which increases the efficiency of emulsification, does not heat up the operative site and lowers the time of operation.

OBJECTS OF THE INVENTION

An object of the present invention is to provide an improved ultrasonic surgical instrument for use in debridement of wounds.

A more particular object of the present invention is to provide such an instrument in the form of a probe that may be used in conjunction with ultrasonic surgical aspirators to debride wounds.

Another relatively specific object of the present invention is to provide an improved ultrasonic surgical instrument with a form that enhances surgical efficiency and reduces the time required to complete at least some kinds of debridement procedures.

It is a further object of the present invention to provide such an improved ultrasonic surgical instrument with irrigation or suction capability.

It is an additional object of the present invention to provide an improved ultrasonic surgical instrument that may be used in debriding deep wounds such as cuts and puncture wounds.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

An ultrasonic probe in accordance with the present invention comprises a shaft having a longitudinal axis and a head disposed at a distal end of the shaft. The head has a cylindrical lateral surface and an end face oriented at least partially transversely relative to the axis. The head has at least three shaping surfaces at a distal end of the cylindrical surface, each of the shaping surfaces extending at a respective acute angle to the axis. Each of the shaping surfaces is intersecting or contiguous with both the cylindrical surface and the end face.

Pursuant to further features of the present invention, the shaping surfaces are angularly or circumferentially spaced from each other about the axis, while the end face has a substantially polygonal shape.

Pursuant to additional feature of the present invention, the end face has a plurality of outer edges each contiguous with two adjacent edges at sharp points, while the shaping surfaces are concave, so that the outer edges of the end face include a plurality of concave edges each along a respective one of the shaping surfaces and further include a plurality of convex edges along the cylindrical surface and between the shaping surfaces.

Pursuant to other features of the present invention, the cylindrical surface is knurled, the end face has at least three arms extending radially outwardly from a hub area, the end face has at least three outer edges each contiguous with two adjacent ones of the outer edges at sharp points, and the shaping surfaces are concave so that the end face has a scalloped shape.

In a specific embodiment of the invention, the shaping surfaces are exactly three in number, while the end face has six outer edges each contiguous with two adjacent ones of the outer edges at sharp points. Preferably, the shaping surfaces are concave. In that event, the outer edges of the probe end face includes three concave edges and three convex edges, the concave edges alternating with the convex edges about the periphery of the end face. Each concave edge is disposed along a respective one of the shaping surfaces, while each convex edge is disposed along the cylindrical surface and between the shaping surfaces.

An ultrasonic probe more generally comprises, in accordance with the present invention, a shaft having a longitudinal axis and a head disposed at a distal end of the shaft. The head has (a) at least one lateral surface that is oriented substantially parallel to the axis, (b) an end face oriented at least partially transversely relative to the axis, and (c) a plurality of shaping surfaces each extending at a respective acute angle to the axis and each intersecting or contiguous with the lateral surface and the end face. The end face has a substantially polygonal shape.

The shaping surfaces may be angularly or circumferentially equispaced from each other about the axis of the probe, while the end face may have six outer edges each contiguous with two adjacent ones of the outer edges at sharp points.

In additional aspects of the present invention, the lateral surface is knurled, the end face has at least three arms extending radially outwardly from a hub area, the end face has at least three outer edges each contiguous with two adjacent ones of the outer edges at sharp points, and the shaping surfaces are concave so that the end face has a scalloped shape.

Where the shaping surfaces are concave, the outer edges include multiple concave edges each along a respective one of the shaping surfaces and further including multiple edges between the shaping surfaces.

BRIEF DESCRIPTION OF THE DRAWING

The sole FIGURE of the drawing is a perspective view of an ultrasonic wound debrider probe in accordance with the present invention.

DETAILED DESCRIPTION

An ultrasonic probe as shown in the drawing includes a shaft 12 having a longitudinal axis 14. At a proximal end of the shaft is provided a screw-type connector 15 for coupling the probe to an ultrasonic transducer assembly in a handpiece (neither shown). A cylindrical or barrel-shaped head 16 is disposed at a distal end of shaft 12. Head has a knurled cylindrical lateral surface 18 and an end face 20 oriented transversely or perpendicularly to axis 14. Head 16 is formed with three concave shaping surfaces 22 at a distal end of lateral surface 18. Each of the shaping surfaces extends at a respective acute angle to axis 14. Accordingly, each shaping surface 22 is inclined relative to lateral surface 18 and end face 20. Each shaping surface 22 intersects or is contiguous with cylindrical surface 18 along an arcuate groin line 24. Each shaping surface 22 intersects or is contiguous with end face 20 along a concave edge 26.

Shaping surfaces 22 are angularly or circumferentially spaced from each other about axis 14, so that end face 20 is bounded not only by concave edges 26 but also by convex edges 28 in the form of circular sections. Concave edges 26 and convex edges 28 are collectively outer edges of end face 20. Each concave outer edge 26 is contiguous with two adjacent convex outer edges 28 at a pair of sharp points 30. Similarly, each convex outer edge 28 is contiguous with two adjacent concave outer edges 26 at sharp points 30.

End face 20 has a generally polygonal shape. In other words, rather than being characterized by a smoothly continuous outer edge such as a circle, an ellipse, or oval, the periphery of end face 20 is characterized by a plurality of sharp points where smoothly continuous edges 26 and 28 meet or join one another.

Accordingly, end face 20 has a plurality of outer edges 26 and 28 each contiguous with two adjacent edges 28 and 26 at sharp points. Shaping surfaces 22 are concave, so that the outer edges of end face 20 include a plurality of concave edges 26 each along a respective one of the shaping surfaces 22 and further include a plurality of convex edges 28 along the lateral surface 18 and between adjacent shaping surfaces 22.

As indicated above, cylindrical lateral surface 18 is knurled, that is, formed with a dense array of projections and recesses.

End face 20 has a scalloped shape with three arms 32 extending radially outwardly from a hub area 34. Hub area 34 is pierced by a distal end of a longitudinal channel or bore 36 extending through shaft 12 for purposes of delivering a liquid coolant to a surgical site.

In the illustrated embodiment, the shaping surfaces 22 are exactly three in number, while end face 20 has six outer edges 26 and 28 each contiguous with two adjacent ones of the outer edges at sharp points 30. The shaping surfaces shape the end face 20 and provide it with multiple sharp edges 26 and 28 and points 30 that aid in tissue fragmentation and would debridement.

It is possible to provide four or more shaping surfaces 22 of even fewer shaping surfaces than three, three is considered an optimal number. While the shaping surfaces 22 may be planar or convex, concave surfaces are considered best.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An ultrasonic probe comprising:
    a shaft having a longitudinal axis; and
    a head disposed at a distal end of said shaft,
    said head having a lateral cylindrical surface and a substantially planar end face oriented substantially perpendicularly to said axis, said end face consisting of a single continuous and unitary substantially planar surface,
    said head having at least three concave shaping surfaces at a distal end of said cylindrical surface,
    each of said shaping surfaces intersecting or contiguous with said cylindrical surface and said end face.

2. The probe defined in claim 1 wherein said shaping surfaces are angularly or circumferentially spaced from each other about said axis and symmetrically disposed about said axis.

3. The probe defined in claim 2 wherein said end face has a generally polygonal shape.

4. The probe defined in claim 3 wherein said shaping surfaces are exactly three in number, said end face having six outer edges each contiguous with two adjacent ones of said outer edges at sharp points.

5. The probe defined in claim 4 wherein said outer edges include three concave edges each along a respective one of said shaping surfaces, said outer edges further including three convex edges along said cylindrical surface and between said shaping surfaces.

6. The probe defined in claim 2 wherein said end face has a plurality of outer edges each contiguous with two adjacent edges at sharp points, said outer edges including a plurality of concave edges each along a respective one of said shaping surfaces, said outer edges further including a plurality of convex edges along said cylindrical surface and between said shaping surfaces.

7. The probe defined in claim 1 wherein said cylindrical surface is knurled.

8. The probe defined in claim 1 wherein said end face has at least three arms extending radially outwardly from a hub area.

9. The probe defined in claim 1 wherein said end face has at least three outer edges each contiguous with two adjacent ones of said outer edges at sharp points.

10. The probe defined in claim 1 wherein said shaping surfaces are concave, said end face having a scalloped shape.

11. An ultrasonic probe comprising:
a shaft having a longitudinal axis; and
a head disposed at a distal end of said shaft,
said head having at least one lateral surface, said lateral surface being oriented substantially parallel to said axis,
said head having a substantially planar end face oriented substantially perpendicularly to said axis, said end face consisting of a single continuously planar and unitary surface,
said head having a plurality of shaping surfaces, each of said shaping surfaces extending at a respective acute angle to said axis, each of said shaping surfaces intersecting or contiguous with said lateral surface and said end face,
said end face having a generally polygonal shape,
said shaft having a longitudinal channel or bore that intersects and opens onto said end face.

12. The probe defined in claim 11 wherein said shaping surfaces are angularly or circumferentially spaced from each other about said axis and symmetrically disposed about said axis.

13. The probe defined in claim 11 wherein said shaping surfaces are angularly or circumferentially equispaced from each other about said axis.

14. The probe defined in claim 11 wherein said end face has six outer edges each contiguous with two adjacent ones of said outer edges at sharp points.

15. The probe defined in claim 11 wherein said shaping surfaces are concave, said outer edges including multiple concave edges each along a respective one of said shaping surfaces, said outer edges further including multiple edges between said shaping surfaces.

16. The probe defined in claim 11 wherein said end face has a plurality of outer edges each contiguous with two adjacent edges at sharp points, said shaping surfaces being concave, said outer edges including a plurality of concave edges each along a respective one of said shaping surfaces, said outer edges further including a plurality of edges along said lateral surface and between said shaping surfaces.

17. The probe defined in claim 11 wherein said lateral surface is knurled.

18. The probe defined in claim 11 wherein said end face has at least three arms extending radially outwardly from a hub area.

19. The probe defined in claim 11 wherein said end face has at least three outer edges each contiguous with two adjacent ones of said outer edges at sharp points.

20. The probe defined in claim 11 wherein said shaping surfaces are concave, said end face having a scalloped shape.

21. An ultrasonic probe comprising:
an elongate probe shaft having a proximal end and a distal end;
a connector at said proximal end of said shaft; and
a head at said distal end of said shaft, said head comprising:
a cylindrical surface having an axis,
a substantially polygonal and substantially planar end face oriented substantially perpendicularly to said axis, and
at least three shaping surfaces each defined by a base edge and an arcuate edge meeting or intersecting the respective base edge at opposite ends thereof, each of said shaping surfaces being contiguous along the respective base edge with said end face and contiguous along the respective arcuate edge with said cylindrical surface.

22. The probe defined in claim 21 wherein said end face has three main edges, said end face having truncated corners forming three ancillary edges each extending between two respective ones of said main edges, said ancillary edges each being substantially shorter than said main edges.

23. The probe defined in claim 22 wherein each of said three main edges has an arcuate form, curving inwardly towards the others of said three main edges.

24. The probe defined in claim 21 wherein said shaft has a longitudinal channel or bore that intersects said end face.

25. The probe defined in claim 21 wherein said cylindrical surface is knurled.

26. An ultrasonic probe comprising:
a shaft; and
a cylindrical head disposed at a distal end of said shaft, said head having a cylindrical lateral surface, said shaft and said head having a common longitudinal axis,
said head having exactly one substantially planar end face oriented substantially perpendicularly to said axis,
said head being formed with a plurality of shaping surfaces at a distal end of said cylindrical lateral surface, each of said shaping surfaces being contiguous with said cylindrical lateral surface and said end face along respective common edges.

27. The probe defined in claim 26 wherein said shaping surface are disposed on an outer side of said head and are all spaced from one another about said axis.

28. The probe defined in claim 26 wherein said cylindrical lateral surface is knurled.

29. The probe defined in claim 26 wherein said shaft and said head are provided with a longitudinal bore or channel that has a distal opening at said end face.

30. The probe defined in claim 26 wherein said shaping surfaces are three in number and wherein said end face is defined by six edges, three of said edges also serving as edges of respective ones of said shaping surfaces, another three of said edges also serving as edges of said cylindrical lateral surface.

31. The probe defined in claim 26 wherein said end face has a scalloped shape with three arms extending radially, outwardly from a hub area.

32. The probe defined in claim 26 wherein said shaping surfaces are exactly three in number, while said end face has six outer edges each contiguous with two adjacent ones of the outer edges at sharp points.

33. The probe defined in claim 26 wherein each shaping surface is concave and intersects or is contiguous with said cylindrical lateral surface along an arcuate groin line, each of said shaping surfaces intersecting or being contiguous with said end face along a concave edge.

* * * * *